United States Patent [19]

Takahashi et al.

[11] Patent Number: 5,266,703
[45] Date of Patent: Nov. 30, 1993

[54] OPTICALLY ACTIVE ISOXAZOLE DERIVATIVES

[75] Inventors: Takashi Takahashi, Kanagawa; Kazuhiko Sakaguchi, Osaka, both of Japan

[73] Assignee: Daiso Co., Ltd., Osaka, Japan

[21] Appl. No.: 906,347

[22] Filed: Jun. 30, 1992

Related U.S. Application Data

[62] Division of Ser. No. 644,779, Jan. 23, 1991, Pat. No. 5,198,588.

Foreign Application Priority Data

Jan. 25, 1990 [JP] Japan .................................. 2-15329

[51] Int. Cl.$^5$ ............................................. C07D 261/20
[52] U.S. Cl. ................................................. 548/241
[58] Field of Search .......................................... 548/241

[56] References Cited

U.S. PATENT DOCUMENTS 4,430,354  2/1984  Boden et al. ........................... 426/536

OTHER PUBLICATIONS

CA 101:23169e Intramolecular . . . $PGF_{2\alpha}$. Kozikowski et al., p. 572, 1984.
J. Org. Chem., Kozikowski et al., 49(13), 2301-9, 1984.
CA 116:128906f Optically . . . Preparation. Takahashi et al., 1992.

*Primary Examiner*—Mary C. Lee
*Assistant Examiner*—Joseph K. McKane
*Attorney, Agent, or Firm*—Armstrong, Westerman, Hattori, McLeland & Naughton

[57] ABSTRACT

The present invention relates to novel optically active isoxazole derivatives represented by general formula:

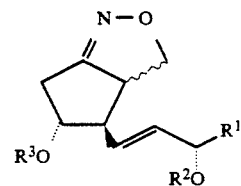

[XI]

which are useful as intermediates for synthesis of prostaglandin and a process for producing the same as well as novel aldehyde compounds represented by general formula:

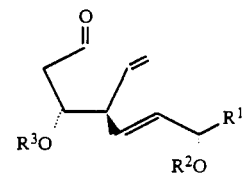

[IX]

which are intermediates for preparing the compounds [XI] described above and a process for preparation thereof. In the compounds shown by these formulae, $R^1$ represents an alkyl group or a cycloalkyl group which may have an alkoxy group or a group shown by -Ra-A-B (wherein Ra is an alkyl group; A is a hetero atom or an single bond; and B is an aromatic or hetero ring which may have a substituent(s)); and $R^2$ and $R^3$, which may be the same or different, each represents an aralkyl group, a silyl group or an acyl group.

3 Claims, 3 Drawing Sheets

OPTICALLY ACTIVE ISOXAZOLE DERIVATIVES

This is a division of application Ser. No. 07/644,779 U.S. Pat. No. 5,198,588 filed Jan. 23, 1991.

BACKGROUND OF THE INVENTION

1. Field of the Invention

The present invention relates to novel optically active isoxazole derivatives represented by general formula:

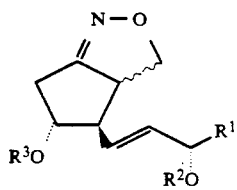

which are useful as intermediates for synthesis of prostaglandin and a process for producing the same as well as intermediates for preparing the compounds [XI] described above and a process for preparation thereof. The optically active isoxazole derivatives [XI] in accordance with the present invention are then led to optically active 2-methylenecyclopentanone derivatives represented by general formula:

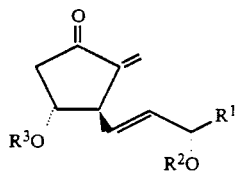

which are important intermediates for synthesis of prostaglandins developed by G. Stork et al. (G. Stork, M. Isobe, J. Am. Chem. Soc., 97, 4745 (1975)). The 2-methylenecyclopentanone derivatives are further led to prostaglandin according to the method of Stork et al. described above.

In the formulae described above, $R^1$ represents an alkyl group or a cycloalkyl group which may have an alkoxy group or a group shown by -Ra-A-B (wherein Ra is an alkyl group; A is a hetero atom or an single bond; and B is an aromatic or hetero ring which may have a substituent(s)); and $R^2$ and $R^3$, which may be the same or different, each represents an aralkyl group, a silyl group or an acyl group.

Prostaglandin (PGF and PGE) is a series of compounds having extremely potent physiological activities which is formed in vivo by chemical conversion of higher unsaturated fatty acids such as arachidonic acid, etc. by the action of enzyme for synthesis of prostaglandin and has the following chemical structures.

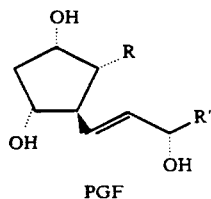
PGF

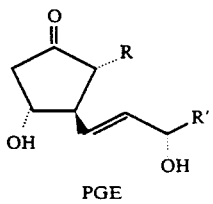
PGE

It is known that in natural prostaglandin, R' is $n-C_5H_{11}-$ and R is $-(CH_2)_6COOH$ or $-CH_2CH=CH(CH_2)_3COOH$ in the formulae above. It is also known that it is important for the group R' to be oleophilic in exhibiting its physiological activities. During the course of development and research on prostaglandin for its application to drugs, it has further been revealed that an alkyl group, a cycloalkyl group or an aralkyl group having 4 to 10 carbon atoms are effective as the group R'; an alkyl group such as pentyl, isopentyl, 2,2-dimethylpentyl, hexyl, 2-hexyl, heptyl, 2-ethoxy-1,1-dimethylethyl, 5-methoxy-1-methylpentyl, etc.; a cycloalkyl group such as cyclopentyl, 3-ethylcyclopentyl, 4-propylcyclohexyl, etc.; and groups such as phenyloxymethyl, 3-trifluoromethylphenyloxymethyl, 2-chlorothiophen-5-yloxymethyl, furan-2-yl-2-ethyl, etc. exert on potent physiological activities. The compounds of the present invention are useful as starting materials which can introduce substituents including these organic groups into the desired compounds.

2. Description of the Prior Art

As routes for preparing optically active prostaglandin, a process starting from Corey lactone and a process starting from 4-hydroxycyclopentenone are hitherto known. However, according to the former process, many steps should be required and as a matter of course, yield of the final product decreases. In the latter process, a problem that it is relatively difficult to set reaction conditions for preventing side reactions but predominating the main reaction over the side ones remains unsolved. The aforesaid process developed by G. Stork et al., namely, the process which comprises preparing 2-methylenecyclopentanone derivatives [XIII] as intermediates and leading the intermediates to prostaglandin is useful in that stable compounds [XIII] are used as intermediates; however, the intermediates [XIII] obtained by this process take a racemic form but no optically active compounds are obtained.

As a result of extensive investigations to solve the problems described above, the present inventors have found a process for preparing optically active 2-methylenecyclopentanone derivatives [XIII] in a simple manner and high yield which are key intermediates for production of prostaglandin. The present invention thus provides novel intermediates obtained during the course of preparing the compounds [XIII] and a process for preparation thereof.

SUMMARY OF THE INVENTION

The optically active isoxazole derivatives in accordance with the present invention possess a chemical structure represented by general formula:

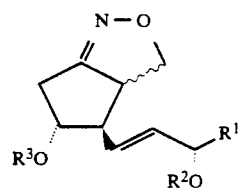

wherein $R^1$ represents an alkyl group or a cycloalkyl group which may have an alkoxy group or a group shown by -Ra-A-B (wherein Ra is an alkyl group; A is a hetero atom or an single bond; and B is an aromatic or hetero ring which may have a substituent(s)); and $R^2$ and R³, which may be the same or different, each represents an aralkyl group, a silyl group or an acyl group.

The optically active aldehyde compounds which are useful for preparing the optically active isoxazole derivatives [XI] described above have a chemical structure represented by general formula:

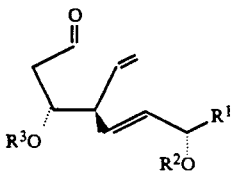

[IX]

wherein R¹, R² and R³ have the same significances as defined above.

For preparing the optically active isoxazole derivatives [XI] described above, optically active oxime compounds represented by general formula:

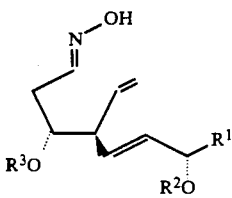

[X]

wherein R¹, R² and R³ have the same significances as defined above, are subjected to intramolecular cyclization.

To prepare the optically active oxime compounds [X] used in the process above, optically active vinyl compounds represented by general formula:

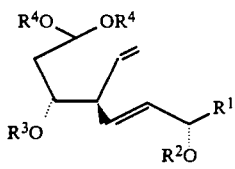

[VIII]

are hydrolyzed to form the optically active aldehyde compounds represented by general formula:

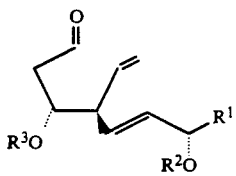

[IX]

in the formulae above, R¹, R² and R³ have the same significances as defined above; R⁴ represents an alkyl group and both R⁴ groups may be combined with each other to form a ring. The aldehyde compounds [IX] are converted into the optically active oxime compounds [X].

To prepare the optically active vinyl compounds [VIII] used in the process described above, optically active hydroxyethyl compounds represented by general formula:

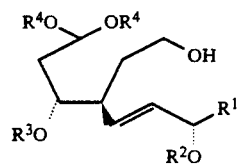

[VII]

wherein R¹, R², R³ and R⁴ have the same significances as defined above, are dehydrated.

To prepare the optically active hydroxyethyl compounds [VII] used in the process described above, optically active ester compounds represented by general formula:

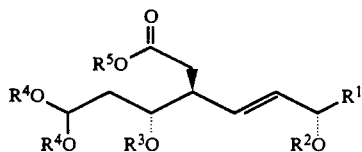

[VI]

wherein R¹, R², R³ and R⁴ have the same significances as defined above; and R⁵ represents an alkyl group, are reduced.

To prepare the optically active ester compounds [VI] used in the process described above, optically active 4-en-6-ol compounds represented by general formula:

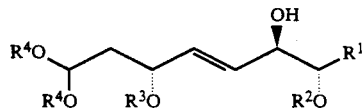

[V]

are reacted with trialkyl orthoacetates represented by general formula:

$$CH_3C(OR^5)_3$$

in the formulae above, R¹, R², R³, R⁴ and R⁵ have the same significances as defined above, followed by intramolecular rearrangement.

To prepare the optically active 4-en-6-ol compounds [V] used in the process described above, optically active 4-yn-6-ol compounds represented by general formula:

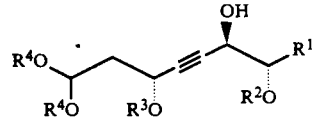

[IIIb]

wherein R¹, R², R³ and R⁴ have the same significances as defined above, are partially reduced.

To prepare the optically active 4-yn-6-ol compounds [IIIb] used in the process described above, optically active 4-yn-6-one compounds represented by general formula:

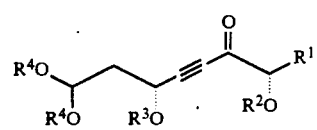

[IV]

wherein R¹, R², R³ and R⁴ have the same significances as defined above, are reduced.

To prepare the optically active 4-yn-6-one compounds [IV] used in the process described above, optically active dibromo compounds represented by general formula:

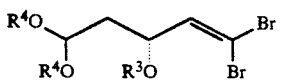

are reacted with optically active aldehyde compounds represented by general formula:

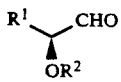

to form optically active 4-yn-6-ol compounds represented by general formula:

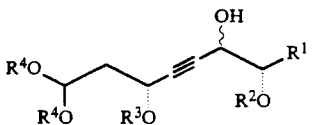

in the formulae above, $R^1$, $R^2$, $R^3$ and $R^4$ have the same significances as defined above. The 4-yn-6-ol compounds [IIIa] are then oxidized.

PREFERRED EMBODIMENTS OF THE INVENTION

Figure 1:
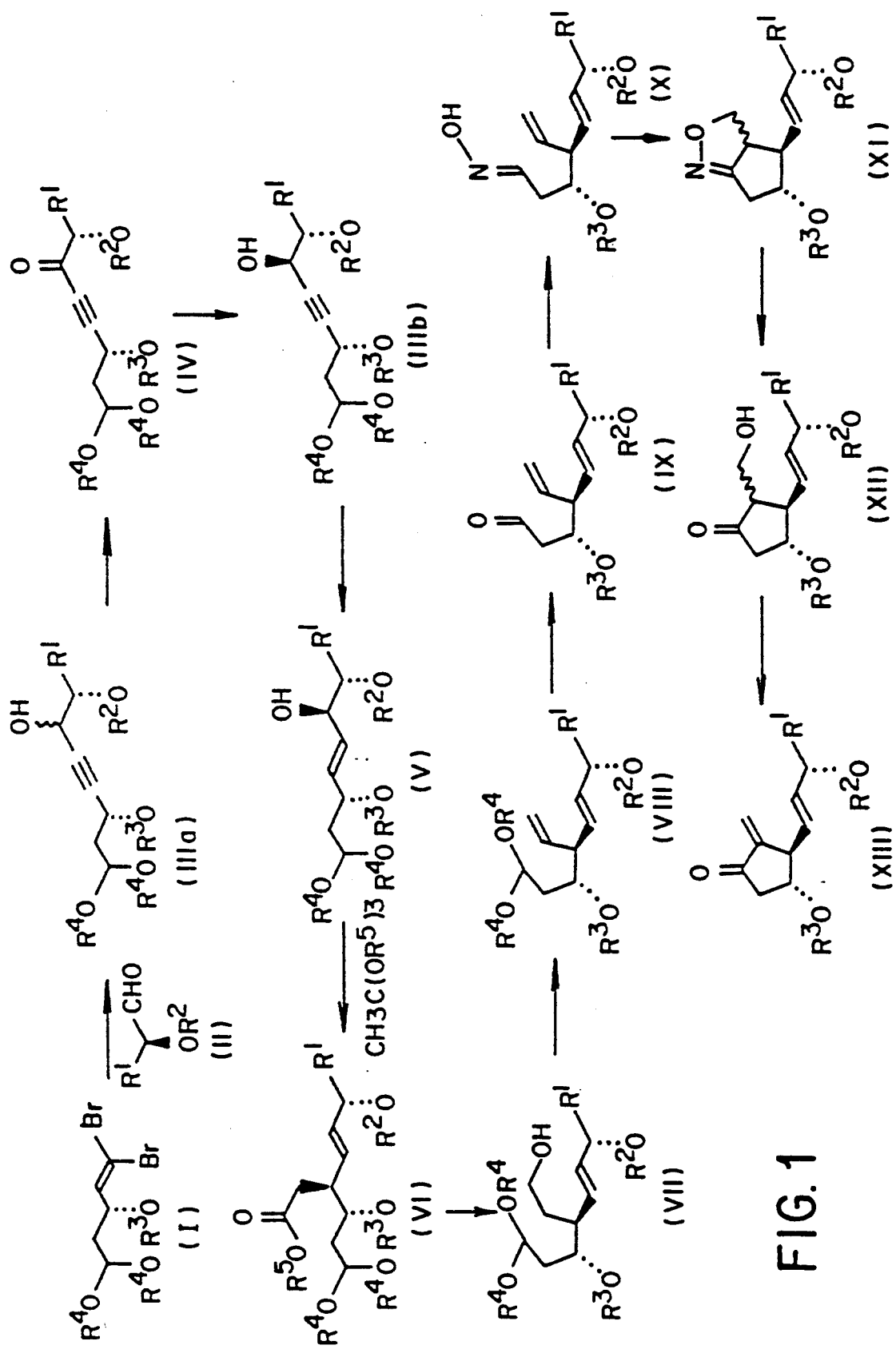
FIG. 1 is a flow sheet showing the reaction route in the present invention.
Figure 2:
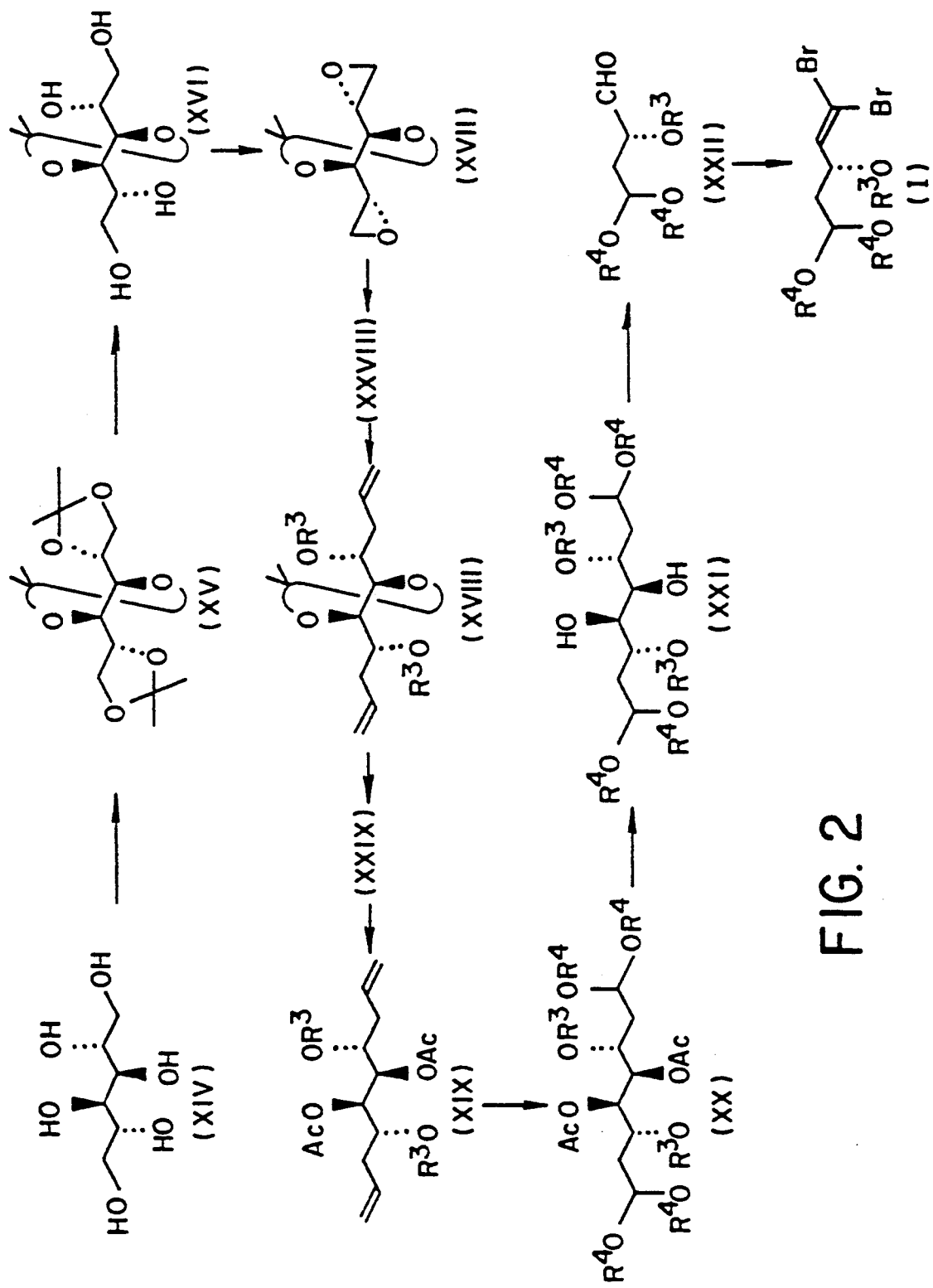
FIGS. 2 and 3 are flow sheets showing steps for preparing starting materials.
Figure 3:
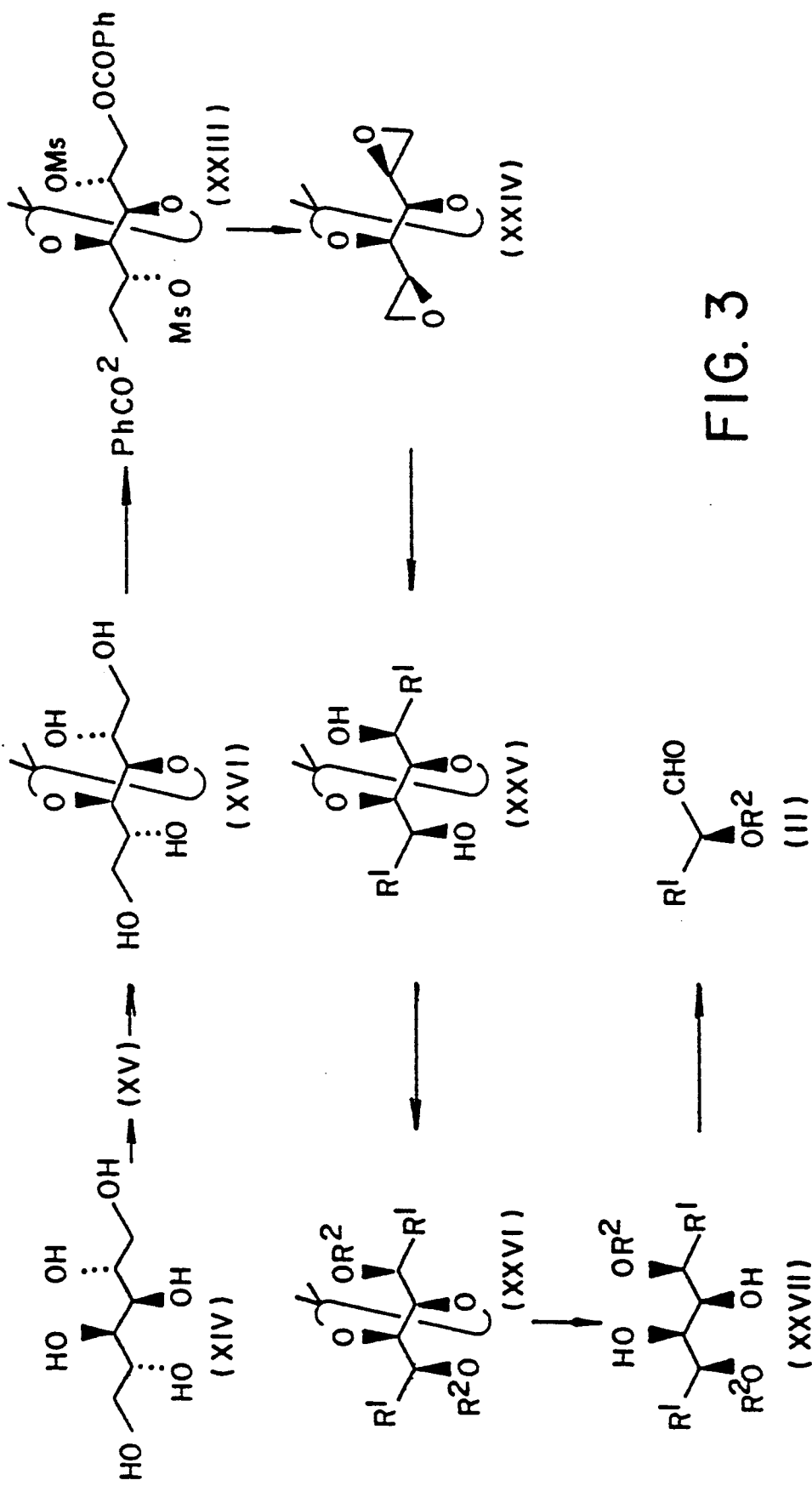

The optically active isoxazole derivatives [XI], intermediates for preparation thereof, optically active 2-methylenecyclopentanone derivatives [XIII] derived from the intermediates and processes for preparing these compounds in accordance with the present invention are shown in Reaction Route 1.

In the present invention, definitions of the respective compounds represented by general formulae described above are explained below.

In each of the compounds described above, group $R^1$ represents (a) an alkyl group or a cycloalkyl group which may have an alkoxy group, or (b) a group shown by -Ra-A-B (wherein Ra is an alkyl group; A is a hetero atom or an single bond; and B is an aromatic or hetero ring which may have a substituent(s)); and $R^2$ and $R^3$, which may be the same or different, each represents an aralkyl group, a silyl group or an acyl group. Examples of the alkyl group or cycloalkyl group in (a) described above include straight or branched alkyl or cycloalkyl groups such as methyl, ethyl, propyl, isopropyl, butyl, isobutyl, pentyl, isopentyl, 2,2-dimethylpentyl, hexyl, 2-hexyl, heptyl, 2-heptyl, octyl, 2-octyl, nonyl, 2-nonyl, decyl, 2-decyl, undecyl, 2-undecyl, dodecyl, 2-ethoxy-1,1-dimethylethyl, 5-methoxy-1-methylpentyl, cyclopentyl, 3-ethylcyclopentyl, cyclohexyl, 2-methylcyclohexyl, 4-n-propylcyclohexyl, etc. As the alkyl group in (a) described above, straight or branched alkyl groups having 4 to 10 carbon atoms are preferred. Of these groups, n-pentyl is particularly preferred. Examples of the group -Ra-A-B in (b) described above include phenyloxymethyl, 3-trifluoromethylphenyloxymethyl, 2-chlorothiophen-5-yl-oxymethyl, furan-2-yl-ethyl, etc.

In the respective compounds, each of $R^2$ and $R^3$ independently represents an aralkyl group, a silyl group or an acyl group. The groups $R^2$ and $R^3$ are appropriately chosen from groups which function as protective groups for hydroxy group and are adapted for reaction conditions of Reaction Route 1. Specific examples of the aralkyl group include benzyl, p-methoxybenzyl, 1-phenethyl groups, etc. Specific examples of the silyl group are dimethyltriphenylmethylsilyl, di-tert-butylmethylsilyl, tert-butyldiphenylsilyl, etc. Specific examples of the acyl group include acetyl, propionyl, n-butyryl, n-valeryl, caproyl, benzoyl, etc. Benzyl group is particularly preferred as $R^2$ and $R^3$.

The alkyl group $R^4$ is appropriately chosen from groups which function as protective groups for carbonyl group in the aldehyde and are also adapted for reaction conditions of Reaction Route 1. Specific examples of the alkyl group are straight or branched alkyl groups such as methyl, ethyl, n-propyl, isopropyl, n-butyl, sec-butyl, tert-butyl, n-pentyl, etc. The two $R^4$ groups may be combined with each other to form a ring such as a cyclic acetal structure.

Examples of the alkyl group $R^5$ include straight or branched alkyl groups such as methyl, ethyl, n-propyl, isopropyl, n-butyl, sec-butyl, tert-butyl, n-pentyl, etc.

Prefered embodiments of Reaction Route 1 are described in more detail.

(i) Firstly, the optically active dibromo compounds [I] are reacted with the optically active aldehyde compounds [II] to give the optically active 4-yn-6-ol compounds [IIIa].

In this step, the dibromo compounds [I] are firstly reacted with about 2 equivalents of bases to convert into acetylene derivatives. The derivatives are then reacted with the optically active aldehyde compounds [II], with or without isolation.

As the bases used herein, alkyl lithium reagents such as methyl lithium, n-butyl lithium, sec-butyl lithium, tert-butyl lithium, etc. are preferred. It is preferred to use non-protonic ethereal solvent such as ethyl ether, tetrahydrofuran, ethylene glycol dimethyl ether, etc. as a reaction solvent, singly or as admixture. The reaction is carried out at a low temperature, preferably at a temperature below $-40°$ C. After dropwise adding the bases to the dibromo compounds [I], the resulting mixture is stirred at the same temperature for 15 to 60 minutes. After the aldehyde compounds [II] are dropwise added to the reaction mixture, the mixture is stirred at the same temperature for 10 to 30 minutes.

(ii) The optically active 4-yn-6-ol compounds [IIIa] obtained in the above step is oxidized to give the optically active 4-yn-6-one compounds [IV].

In this step, the hydroxy group of the 4-yn-6-ol compounds [IIIa] is oxidized to the ketone group. For oxidation of the 4-yn-6-ol compounds [IIIa], there are may methods. Representative examples are (a) oxidation with metal reagents such as oxidation with chromic acid, oxidation with manganic acid, etc., (b) Swern's oxidation, (c) Corey-Kim oxidation, etc.

(a) In the oxidation using metal reagents, chromic acid, potassium bichromate, sodium bichromate, manganese dioxide, potassium permanganate, sodium permanganate, PCC (pyridinium chlorochromate), PDC (pyridinium dichromate), etc. are used as reagents. As a reaction solvent, methylene chloride, chloroform, carbon tetrachloride, or the like is generally used.

(b) The Swern's oxidation is a method using dimethylsulfoxide (Synthesis, 165, (1978)). According to this method, an acid chloride such as oxalyl chloride, etc. or an acid anhydride such as trifluoroacetic anhydride, etc. is reacted with dimethylsulfoxide to form the sulfonium salt, the salt is reacted with the 4-yn-6-ol compound [IIIa] and the product is then treated with a base to convert into the 4-yn-6-one compound [IV]. It is preferred to use as a reaction solvent a non-protonic solvent such as methylene chloride, chloroform, carbon tetrachloride, etc. which are made anhydrous. The reaction is carried out at a low temperature below $-40°$ C., preferably at about $-78°$ C.

(c) In the Corey-Kim oxidation, N-chlorosuccinimide and dimethylsulfide are used (J. Am. Chem. Soc., 94, 7587 (1972)). The oxidation can be attained also by this method.

(iii) The ketone group of the optically active 4-yn-6-one compound [IV] obtained in the step described above is asymmetrically reduced to give the optically active 4-yn-6-ol compound [IIIb].

As a reducing reagent used in this reaction, zinc borohydride is preferred. This reagent is used generally in the form of a diethyl ether solution in a concentration of 0.1 to 0.5 mol/l. The reaction can be carried out by dropwise adding the reducing reagent to the 4-yn-6-one compound [IV] in 1 to 2 equivalents based on the compound [IV] at a low temperature, preferably $-20°$ to $-40°$ C. in a nitrogen atmosphere and stirring the reaction mixture for further 5 to 30 minutes. It is preferred to use as a reaction solvent a non-protonic nonpolar solvent such as diethyl ether, tetrahydrofuran, etc., singly or as admixture.

(iv) The optically active 4-yn-6-ol compound [IIIb] obtained in the step described above is partially reduced to give the optically active 4-en-6-ol compound [V].

This step comprises partially reducing the carbon-carbon triple bond of the 4-yn-6-ol compound [IIIb] to convert into the carbon-carbon double bond, whereby the trans olefin compound [V] is obtained. As a reducing reagent used in this reaction, lithium aluminum hydride is preferred. This partial reduction can be carried out by adding the 4-yn-6-ol compound [IIIb] to a suspension containing 1 to 3 equivalents of lithium aluminum hydride based on the compound [IIIb] at a low temperature, preferably at about $0°$ C. and then stirring for 10 to 30 minutes under reflux. It is preferred to use as a reaction solvent a non-protonic nonpolar solvent such as diethyl ether, tetrahydrofuran, etc., singly or as admixture.

(v) Trialkyl orthoacetates $CH_3C(OR^5)_3$ are reacted with the optically active 4-en-6-ol compound [V] obtained in the step described above followed by intramolecular rearrangement. The optically active ester compound [VI] is thus obtained.

This step comprises acylation of the hydroxy group in the 4-en-6-ol compound [V] through the reaction with the trialkyl orthoacetate and intramolecular rearrangement thereby to convert the compound [V] into the ester compound [VI].

The reaction can be carried out by dissolving 1 to 5 equivalents of the trialkyl orthoacetate and 0.01 to 0.3 equivalent (catalytic amount) of an acid in a solvent based on the compound [V] and heating the mixture at $140°$ to $180°$ C. for 5 to 30 minutes. As the trialkyl orthoacetate, trimethyl orthoacetate, triethyl orthoacetate, tripropyl orthoacetate, tributyl orthoacetate, etc. are preferred. As the acid used in a catalytic amount, hexanoic acid, heptanoic acid, octanoic acid, nonanoic acid, etc. are preferred. As a reaction solvent, xylene is usually used.

(vi) The optically active ester compound [VI] obtained in the step described above is reduced to give the optically active hydroxyethyl compound [VII].

In this step, the alkyl ester moiety of the ester compound [VI] is reduced to the primary alcohol.

As a reducing agent, lithium aluminum hydride is preferred. This reaction can be carried out by reacting the ester compound [VI] with 1 to 3 equivalents of lithium aluminum hydride based on the compound [VI] at a temperature of $5°$ to $30°$ C. for 15 to 90 minutes. It is preferred to use as a reaction solvent a non-protonic nonpolar solvent such as diethyl ether, tetrahydrofuran, etc., singly or as admixture.

(vii) The optically active hydroxyethyl compound [VII] obtained in the step described above is dehydrated to give the optically active vinyl compound [VIII].

In this step, the primary alcohol moiety in the hydroxyethyl compound [VII] is converted into the terminal olefin through the dehydration, whereby the vinyl compound [VIII] is obtained. That is, the vinyl compound [VIII] can be obtained by firstly converting the hydroxyethyl compound [VII] into the selenium compound, then oxidizing the selenium compound and causing elimination.

This reaction can be carried out by dropwise adding the hydroxyethyl compound [VII] to a suspension of 1 to 3 equivalents of an aryl selenium cyanide in a medium such as diethyl ether or tetrahydrofuran based on the hydroxyethyl compound [VII] at $5°$ to $30°$ C., then dropwise adding the same quantity of a trialkylphosphine or triphenylphosphine to the mixture, continuing stirring for further 5 to 30 minutes, cooling the reaction solution to about $0°$ C., dropwise adding 10 to 40% hydrogen peroxide solution with stirring, and stirring the mixture for further 1 to 5 hours.

As the aryl selenium cyanide, o-nitrophenyl selenium cyanide, p-nitrophenyl selenium cyanide, etc. are used. As the trialkylphosphine, triethylphosphine, tripropylphosphine, tri-n-butylphosphine, etc. are preferred.

(viii) The optically active vinyl compound [VIII] obtained in the step described above is hydrolyzed to give the optically active aldehyde compound [IX].

The step comprises hydrolysis of the acetal group in the vinyl compound [VIII] in the presence of an acid catalyst to convert into the aldehyde group. This reaction can be carried out by dissolving the vinyl compound [VIII] in a solvent such as mixture of 60 to 90% acetic acid and tetrahydrofuran and stirring the solution at a temperature of $20°$ to $60°$ C. for 1 to 8 hours.

As the acid used in the reaction, in addition to acetic acid, an organic acid such as formic acid, propionic acid, trifluoroacetic acid, etc. and a mineral acid such as hydrochloric acid, sulfuric acid, etc. are preferred.

Subsequent steps (ix) through (xii) are carried out roughly in accordance with the technique developed by Kozikowski et al. (J. Am. Chem. Soc., 104, 4023, (1982)).

(ix) The optically active aldehyde compound [IX] obtained in the step described above is converted into the optically active oxime compound [X].

The reaction is carried out by dissolving the aldehyde compound [IX] in a solution such as pyridine, adding 1 to 1.5 equivalents of hydroxylamine hydrochloride to the solution and stirring the mixture at room temperature for 30 to 90 minutes.

(x) The optically active oxime compound [X] obtained in the step described above is intramolecularly cyclized to the optically active isoxazole derivative [XI].

In this step, the oxime moiety and the olefin moiety in the oxime compound [X] are intramolecularly [3+2] cyclized and added to convert the compound [X] into the isoxazole derivative [XI].

This reaction is carried out by stirring the oxime compound [X] and 0.01 to 0.3 equivalent of triethylamine in a solvent, dropwise adding 1 to 10 equivalents of 5 to 30% sodium hypochlorite to the mixture at a low temperature, preferably at about 0° C., and stirring the mixture at about 0° C. for 30 minutes to 2 hours and at 10° to 30° C. for further 5 to 24 hours. As a reaction solvent, methylene chloride, chloroform, carbon tetrachloride, etc. are preferably used.

(xi) The optically active isoxazole derivative [XI] obtained in the step described above is reduced to give the optically active cyclopentanone derivative [XII].

This reaction is carried out by stirring a mixture of the isoxazole derivative [XI] and a hexane solution of a catalytic amount of inactivated Raney nickel and boron trichloride in 80% methanol aqueous solution for about 3 hours in a hydrogen gas atmosphere.

(xii) The optically active cyclopentanone derivative [XII] obtained in the step described above is dehydrated to give the optically active 2-methylenecyclopentanone derivative [XIII].

This reaction is carried out by dissolving the cyclopentanone derivative [XII] in anhydrous pyridine and reacting the solution with methanesulfonyl chloride at a low temperature, preferably at about 0° C.

The thus obtained optically active 2-methylenecyclopentanone derivative [XIII] can be led to prostaglandin (PGF and PGE described above) according to the prostaglandin synthesis of G. Stork et al. supra.

Next, the respective steps for preparing the optically active dibromo compounds [I] and the optically active aldehyde compound [II] which are starting materials in Reaction Route 1 in preparing the intermediates of the present invention for production of prostaglandin are described below.

The optically active dibromo compound [I] can be prepared by Reaction Route 2.

In the respective compounds in Reaction Route 2, groups $R^3$ and $R^4$ have the same significances as those in Reaction Route 1, and Ac represents acetyl group. Firstly, D-mannitol [XIV] is reacted with acetone in the presence of an acid catalyst to give triacetonide [XV] and the triacetonide [XV] is partially hydrolyzed with hydrated acetic acid to give tetraol [XVI]. After only the two primary hydroxy groups of the resulting tetraol [XVI] are selectively tosylated with tosyl chloride/pyridine, the product is reacted with a base such as potassium carbonate, etc., whereby the tetraol [XVI] is converted into diepoxide [XVII]. The resulting diepoxide [XVII] is reacted with a vinyl anion equivalent such as vinyl Grignard copper (I) to open the two epoxide rings. The thus obtained diene [XXVIII] is reacted with $R^3X$ (wherein X represents chlorine, bromine or iodine) under basic conditions to give diene [XVIII]. Then, the diene [XVIII] is hydrolyzed with hydrated acetic acid and the formed diol [XXIX] is acetylated with pyridine/acetyl chloride to give diacetoxydiene [XIX]. The resulting diacetoxydiene [XIX] is decomposed with ozone and the formed aldehyde is converted into the acetal to protect the aldehyde. The acetyl group in the formed tetramethoxyoctane [XX] is hydrolyzed under basic conditions, whereby the octane [XX] is converted into diol [XXI]. The diol [XXI] is reacted with lead tetraacetate, sodium periodate, etc., whereby the carbon-carbon bond is oxidatively cleaved to convert the diol [XXI] into butanal [XXII]. Then, the butanal [XXII] is reacted with triphenylphosphine and tetrabromomethane. Thus, the dibromo compound [I] which is the starting material of the present invention is obtained.

The optically active aldehyde compound [II] which is another starting material can be prepared according to Reaction Route 3. In the respective compounds in Reaction Route 3, groups $R^1$ and $R^2$ have the same significances as those in Reaction Route 1; Ms represents methylsulfoxy group and Ph represents phenyl group.

Firstly, D-mannitol [XIV] is treated in a manner similar to Reaction Route 2 to give tetraol [XVI]. After only the two primary hydroxy groups in the tetraol [XVI] are selectively benzoylated under basic conditions, the two secondary hydroxy groups are further mesylated, whereby the tetraol [XVI] is converted into acetonide [XXIII]. The resulting acetonide [XXIII] is reacted with potassium carbonate to convert into diepoxide [XXIV]. The diepoxide [XXIV] is further reacted with $R^7MgBr$ (wherein $R^7$ represents a group having carbon atom numbers smaller by one than in $R^1$) in the presence of CuCN or CuI to give diol [XXV]. Then, the diol [XXV] is reacted with $R^2X$ (wherein X represents chlorine, bromine or iodine) under basic conditions to give acetal [XXVI]. After the resulting acetal [XXVI] is hydrolyzed with hydrated acetic acid into diol [XXVII], the diol [XXVII] is oxidized with lead tetraacetate or sodium periodate. The optically active aldehyde compound [II] is thus obtained.

EXAMPLES

In order to demonstrate the technical characteristics of the present invention, Examples of the present invention and Reference Examples for synthesis of starting materials and the like are shown. However, the present invention is not deemed to be limited to these examples. In these Examples and Reference Examples, specific compounds which fall under the groups designated by Roman numbers [I] through [XXIX] are shown by Arabic numbers [1] through [29] corresponding to the Roman numbers above. All % indicating proportion are by weight.

REFERENCE EXAMPLE 1

Synthesis of dibromo compound [1]

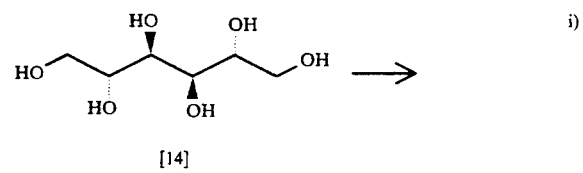

[14]

-continued

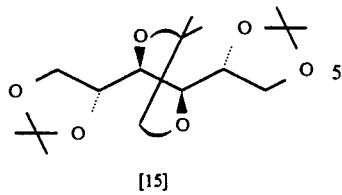

[15]

After 45 g of D-mannitol [14] was vigorously stirred in 1 liter of acetone containing 1 ml of conc. sulfuric acid at room temperature for 3 days, 50 g of potassium carbonate was added to the mixture. Stirring was continued for further one day. The solid matter was removed by filtration with suction and the solvent in the filtrate was distilled off under reduced pressure. Water was added to the resulting residue and the precipitated crystals were taken by suction and filtration to give 45 g of crude product. After the crude product was dissolved in 20 ml of ethanol with heating, the solution was filtered and the filtrate was cooled to room temperature. The precipitated crystals were taken by filtration to give 37.3 g (yield 50%) of (2R,3R,4R,5R) triacetonide [15].

$^1$H NMR (CCl$_4$) δ: 1.40 (6H, s, CH$_3$×2), 1.43 (12H, s, CH$_3$×4), 3.7-4.4 (8H, m, CH$_2$, CH)

ii)

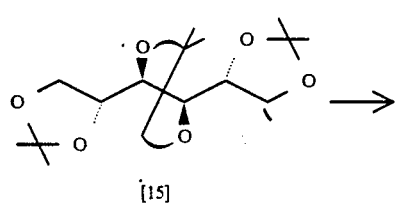

[15]

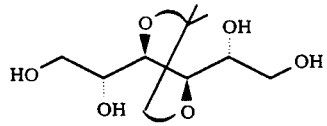

[16]

After 15 g (0.05 mol) of the aforesaid triacetonide [15] was stirred in 50 ml of 70% acetic acid at 40° C. for 3.5 hours, the reaction solution was concentrated at 40° C. under reduced pressure as quickly as possible. Acetone was added to the residue and the precipitated D-mannitol (0.72 g) was filtered off. Acetone was distilled off from the filtrate under reduced pressure to give syrup-like product. The syrup was recrystallized from 50 ml of benzene to give 8.8 g (yield, 80%) of (2R,3R,4R,5R) tetraol [16].

$^1$H NMR (D$_2$O) δ: 1.38 (6H, s, CH$_3$×2), 3.3-4.2 (8H, m, CH$_2$, CH)

iii)

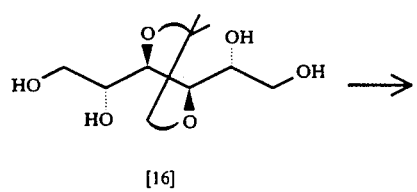

[16]

-continued

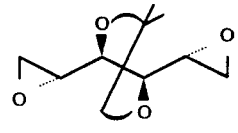

[17]

After 60.4 g (0.32 mol) of p-toluenesulfonyl chloride was added at 0° C. to a solution of 31.8 g (0.14 mol) of (2R,3R,4R,5R) hexane-1,2,5,6-tetraol [16] obtained in a manner similar to the step described above in 124 ml of anhydrous pyridine with stirring, the mixture was stirred at the same temperature for 3 hours and at room temperature for further 2 hours. It was confirmed by thin layer chromatography that the reaction was completed. After 400 ml of diethyl ether was added to the reaction mixture, the resulting mixture was filtered through Celite and the solvent was distilled off under reduced pressure. After 300 ml of methanol and 40.5 g (0.29 mol) of potassium carbonate were added to the residue, the mixture was stirred at room temperature for 4 hours. After 200 ml of diethyl ether was added to the reaction mixture, the resulting mixture was filtered through Celite and the solvent was distilled off under reduced pressure to give 9.18 g of (2R,3R,4R,5R) diepoxide [17]. Yield, 35%.

bp: 85°-90° C.

$^1$H NMR (CDCl$_3$) δ: 1.45 (6H, s), 2.72 (2H, dd, J=3.9, 4.6 Hz), 2.83 (2H, dd, J=4.1, 4.6 Hz), 3.0-3.2 (2H, m), 3.7-3.9 (2H, m)

iv)

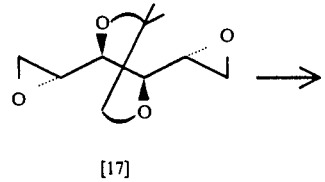

[17]

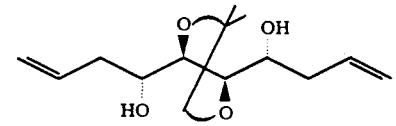

[28]

To a mixture of 327 mg of cuprous cyanide and 200 mf of anhydrous tetrahydrofuran was added 72 ml (0.108 M) of vinyl magnesium chloride solution having a concentration of 1.5 M, which had been separately prepared, at 0° C. over 5 minutes. After stirring for further 5 minutes, a solution of 6.67 g (35.9 mM) of (2R,3R,4R,5R) diepoxide [17] in 20 ml of anhydrous tetrahydrofuran was dropwise added at 0° C. over 10 minutes with stirring. Stirring was continued for further an hour. After it was verified by thin layer chromatography that the reaction was completed, ammonium chloride and saturated sodium chloride aqueous solution were added to the reaction mixture. After stirring for 30 minutes, the reaction mixture was extracted with ethyl ether 3 times. The extracts were combined and washed, in sequence, with 1 N hydrochloric acid, saturated sodium bicarbonate aqueous solution and saturated sodium chloride aqueous solution. After drying over anhydrous magnesium sulfate, the solvent was distilled off under reduced pressure to give 7.38 g (30.5 mM) of (4R,5R,6R,7R) 4,7-dihydroxydeca-1,9-diene [28]. Yield, 85%.

$[\alpha]_D^{25}$: +6.83° (C=1.200, CHCl₃)

¹H NMR (CDCl₃) δ: 1.40 (6H, s), 2.0–2.8 (4H, m), 2.85–3.38 (2H, br s), 3.4–3.85 (4H, m), 5.0–5.3 (4H, m), 5.6–6.15 (2H, m)

¹³C NMR (CDCl₃) δ: 27.0, 38.6, 72.2, 82.7, 108.9, 118.1, 134.3

IR (neat): 3300, 1640, 1070, 915 cm⁻¹

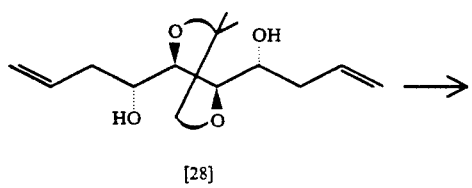

[28]

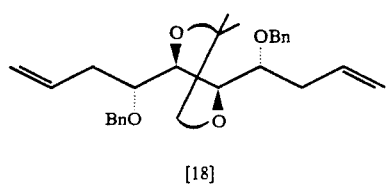

[18]

After 7.38 g (30.5 mM) of (4R,5R,6R, 7R) 4,7-dihydroxydeca-1,9-diene [28] described above was dissolved in 30 ml of anhydrous tetrahydrofuran, a suspension of 0.024 g (1.07 mM) of sodium hydride in 100 ml of anhydrous tetrahydrofuran was dropwise added to the solution under reflux over 15 minutes. After stirring for further an hour under reflux, the mixture was cooled to 0° C. After 132 mg of DC-18-crown ether-6 and 9.3 ml (78 mols) of benzyl bromide were added to the suspension at 0° C., the mixture was refluxed for 4 hours while stirring. After the solvent was distilled off under reduced pressure, 1 N hydrochloric acid was added to the residue followed by extraction with hexane. The extract was sequentially washed with saturated sodium bicarbonate aqueous solution and saturated sodium chloride aqueous solution. After drying over anhydrous magnesium sulfate, the solvent was distilled off under reduced pressure to give 11.3 g (26.8 mM) of (4R,5R,6R,7R) 4,7-dibenzyloxydeca-1,9-diene [18]. Yield, 88%.

¹H NMR (CDCl₃) δ: 1.39 (6H, s), 2.42 (4H, br t, J=6 Hz), 3.60 (2H, m), 4.06 (2H, m), 4.54 (4H, ABq), 4.98–5.22 (4H, m), 5.74–6.03 (2H, m), 7.28 (10H, s)

¹³C NMR (CDCl₃) δ: 27.28, 34.55, 71.79, 79.65, 116.99, 127.33, 127.62, 128.07, 128.85, 134.71, 138.31

IR (neat): 1641, 1089, 1071, 913, 872, 778, 736, 697 cm⁻¹

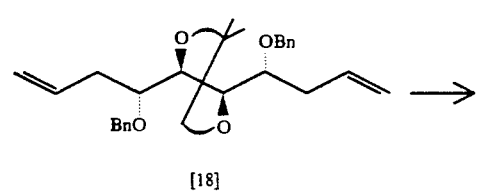

[18]

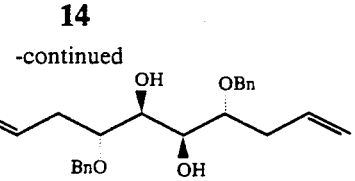

[29]

After 11.3 g (26.8 mM) of (4R,5R,6R, 7R) 4,7-dibenzyloxydeca-1,9-diene [18] described above was heated at 100° C. in 100 ml of 80% acetic acid for 10 hours while stirring, the solvent was distilled off under reduced pressure followed by extraction with diethyl ether. The extract was washed with sodium hydroxide aqueous solution and the aqueous phase was further extracted with diethyl ether. The extracts were combined and washed, in sequence, with 1 N hydrochloric acid, saturated sodium bicarbonate aqueous solution and then saturated sodium chloride aqueous solution, and then dried over anhydrous magnesium sulfate. After the solvent was distilled off under reduced pressure, the residue was subjected to silica gel column chromatography and 8.71 g (22.8 mM) of (4R,5R,6R,7R) 4,7-dibenzyloxydeca-1,9-diene-5,6-diol [29] was obtained from the fraction eluted with diethyl ether:-hexane=1:4. Yield, 85%.

¹H NMR (CDCl₃) δ: 2.40 (4H, br t, J=6 Hz), 3.54–3.92 (4H, m), 4.53, 4.69 (4H, ABq, J=11.2 Hz), 4.97–5.29 (4H, m), 5.56–6.14 (2H, m), 7.32 (10H, s)

IR (neat): 3468, 1640, 1092, 1028, 914, 737, 698 cm⁻¹

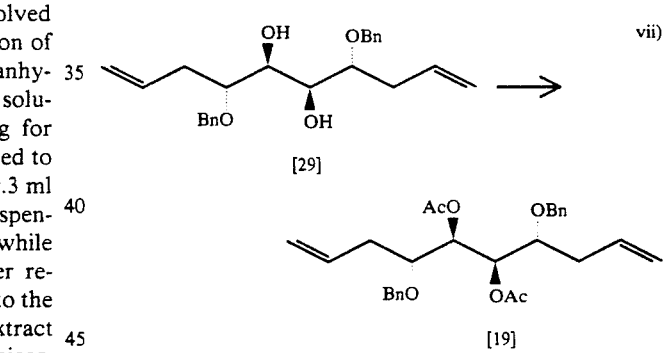

After 8.71 g (22.8 mM) of (4R,5R,6R, 7R) 4,7-dibenzyloxydeca-1,9-diene-5,6-diol [29] described above and 4.33 g (54.8 mM) of pyridine were dissolved in 100 ml of methylene chloride, 4.30 g (54.8 mM) of acetyl chloride was dropwise added to the solution with stirring. The resulting mixture was stirred at 25° C. for 3 hours. The reaction mixture was washed, in sequence, with 0.5 N hydrochloric acid, saturated sodium bicarbonate aqueous solution and saturated sodium chloride aqueous solution. After drying over anhydrous magnesium sulfate, the solvent was distilled off under reduced pressure to give 9.55 g (20.5 mM) of (4R,5R,6R,7R) 5,6-diacetoxy-4,7-dibenzyloxydeca-1,9-diene [19]. Yield, 90%.

¹H NMR (CDCl₃) δ: 2.00 (6H, s), 2.37 (4H, br t, J=6 Hz), 3.58 (2H, br q, J=5 Hz), 4.50 (4H, s), 5.00–5.19 (4H, m), 5.40 (2H, br d, J=3.6 Hz), 5.70–5.95 (2H, m), 7.32 (10H, s)

¹³C NMR (CDCl₃) δ: 21.07, 34.30, 71.31, 72.32, 77.76, 117.84, 128.14, 128.41, 128.67, 134.52, 138.31, 170.53

IR (neat): 1744, 1642, 1370, 1224, 1090, 915, 736, 698 cm⁻¹

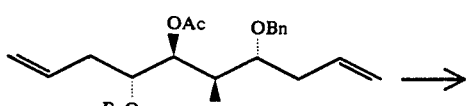

[19]

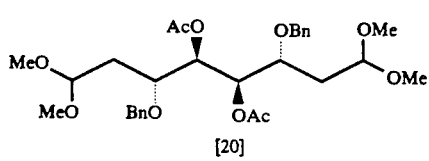

[20]

After 9.55 g (20.5 mM) of (4R,5R,6R, 7R) 5,6-diacetoxy-4,7-dibenzyloxydeca-1,9-diene [19] was dissolved in 950 ml of anhydrous methanol, the solution was cooled to −78° C. While stirring, ozone gas was introduced until the reaction solution was colored blue. Stirring was continued for further 15 minutes at the same temperature. Then, 15 ml of distilled dimethylsulfide was added to the reaction solution. After the reaction solution was reverted to room temperature, stirring was continued for 5 hours. After 0.2 g of p-toluenesulfonic acid was added to the reaction mixture, the mixture was stirred at room temperature for 10 hours. Then 10 g of potassium carbonate was added thereto and the resulting suspension was stirred for 3 hours. The reaction solution was filtered and the filtrate was distilled off under reduced pressure. Diethyl ether and water were added to the residue and the resulting mixture was extracted. The aqueous phase was further extracted with diethyl ether. The extracts were combined and washed with saturated sodium chloride aqueous solution. After the extract was dried over anhydrous magnesium sulfate, the solvent was distilled off under reduced pressure. The residue was subjected to silica gel column chromatography and 8.41 g (15.0 mM) of (3R,4R,5R,6R) 4,5-diacetoxy-3,6-dibenzyloxy-1,1,8,8-tetramethoxyoctane [20] was obtained from the fraction eluted with ethyl acetate:hexane=1:1. Yield, 73%.

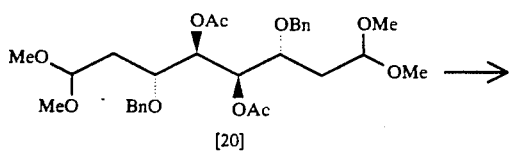

[20]

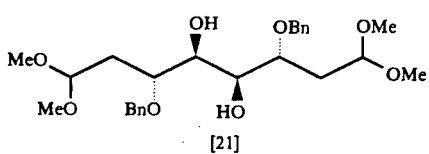

[21]

To 100 ml of methanol were added 9.76 g (17.4 mM) of (3R,4R,5R,6R) 4,5-diacetoxy-3,6-dibenzyloxy-1,1,8,8-tetramethoxyoctane [20] obtained via the same route as described above and 6.17 g (43.5 mM) of potassium carbonate. The mixture was heated for 2 hours under reflux while stirring. After it was confirmed by thin layer chromatography that the reaction was completed, the solvent was distilled off under reduced pressure. Water was added to the residue and the mixture was extracted with diethyl ether. After the extract was washed with saturated sodium chloride aqueous solution and dried over anhydrous magnesium sulfate, the solvent was distilled off under reduced pressure to give 7.55 g (15.8 mM) of (3R,4R, 5R,6R) 3,6-dibenzyloxy-1,1,8,8-tetramethoxyoctane-4,5-diol [21]. Yield, 91%.

$^1$H NMR (CDCl$_3$) δ: 1.77-2.17 (4H, m), 3.03, 3.23 (2H, br d), 3.26 (6H, s), 3.30 (6H, s), 3.64-3.96 (4H, m), 4.38-4.85 (2H, m), 4.63 (4H, s), 7.32 (10H, s)

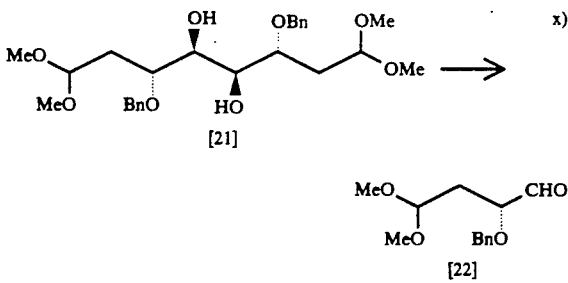

[21]

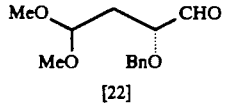

[22]

While stirring, 10.46 g (21.5 mM) of lead tetraacetate was added at 0° C. to a mixture of 7.55 g (15.8 mM) of (3R,4R,5R,6R) 3,6-dibenzyloxy-1,1,8,8-tetramethoxyoctane-4,5-diol [21] described above, 6.52 g (46 mM) of potassium carbonate and 200 ml of anhydrous benzene. The mixture was stirred at 0° C. for 10 minutes. After it was confirmed by thin layer chromatography that the reaction was completed, hexane was added to the reaction mixture. The resulting mixture was filtered through Celite 545 and the filtrate was washed with saturated sodium bicarbonate aqueous solution. The aqueous phase was extracted with diethyl ether. The extracts were combined and washed with saturated sodium chloride aqueous solution. After drying over anhydrous magnesium sulfate, the solvent was distilled off under reduced pressure to give 6.17 g (25.9 mM) of (R) 2-benzyloxy-4,4-dimethoxybutanal [22]. Yield, 82%.

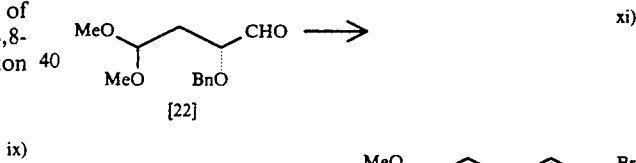

[22]

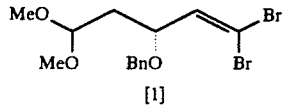

[1]

To a solution of 24.5 g (93.4 mM) of triphenylphosphine in 120 ml of anhydrous methylene chloride was dropwise added 15.4 g (46.5 mM) of tetrabromomethane at 0° C. with stirring. After the mixture was stirred at the same temperature for 10 minutes, a solution of 6.17 g (25.9 mM) of (R) 2-benzyloxy-4,4-dimethoxybutanal [22] described above in 24 ml of anhydrous methylene chloride was added thereto. The solution mixture was reverted to room temperature and stirring was continued at the same temperature for 3 hours. After it was confirmed by thin layer chromatography that the reaction was completed, 800 ml of hexane was added to the reaction mixture. The resulting suspension was filtered through Celite 545 and the filtrate was washed with saturated sodium bicarbonate aqueous solution. The aqueous phase was extracted with diethyl ether. The extracts were combined and washed with saturated sodium chloride aqueous solution. After drying over anhydrous magnesium sulfate, the solvent was distilled off under reduced pressure.

The residue was subjected to silica gel column chromatography and 7.25 g (18.4 mM) of (R) 3-benzyloxy-1,1-dibromo5,5-dimethoxypenta-1-ene [1] from the fraction eluted with diethyl ether:hexane=1:10. Yield, 71%.

[α]$_D^{25}$: +13.78° (C=1.016, CHCl$_3$)

$^1$H NMR (CDCl$_3$) δ: 1.75–2.02 (2H, m), 3.28 (3H, s), 3.30 (3H, s), 4.10–4.80 (4H, m), 6.43 (1H, d, J=8.6 Hz), 7.26 (5H, s)

IR (neat): 1615, 1100–1060, 735, 695 cm$^{-1}$

REFERENCE EXAMPLE 2

Synthesis of optically active aldehyde [2]

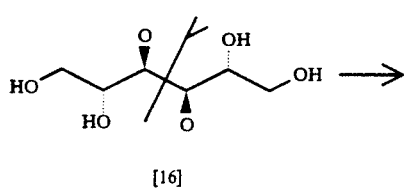

[16]

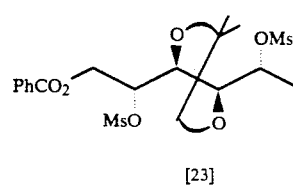

[23]

A mixture of 16 ml (0.138 mol) of benzoyl chloride and 5 ml of anhydrous methylene chloride was dropwise added at −70° C. to a solution of 15.3 g (0.069 mol) of the tetraol [16] obtained from D-mannitol [14] in a manner similar to Reference Example 1 in 55 ml (0.68 mol) of anhydrous pyridine and 50 ml of methylene chloride, over 15 minutes. After completion of the dropwise addition, the mixture was further stirred at −30° C. for an hour at room temperature for 10 hours. After it was confimrmed by thin layer chromatography that the reaction was completed, the solvent was distilled off under reduced pressure. After 11.2 ml (0.144 mol) of methanesulfonyl chloride was added to the residue at 0° C. over 20 minutes, the resulting suspension was stirred at room temperature for 3 days. After it was confimrmed by thin layer chromatography that the reaction was completed, 100 ml of a solvent mixture of ethyl ether:hexane=7:3 (volume) was added to the reaction mixture. This yellow suspension was filtered through Celite 545 and the solvent was distilled off under reduced pressure. The resulting brown residue was diluted with methylene chloride. After the dilution was rendered acidic by adding conc. hydrochloric acid thereto, it was extracted with methylene chloride 3 times. The extract was washed, in sequence, with saturated sodium bicarbonate aqueous solution and saturated sodium chloride aqueous solution and then dried over anhydrous magnesium sulfate. The solvent was distilled off under reduced pressure to give 42 g of brown semi-solid (2R,3S,4S,5R) acetonide [23].

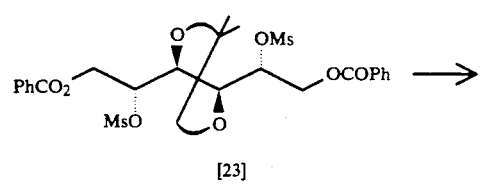

[23]

ii)

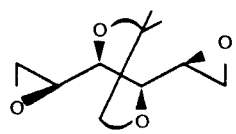

[24]

(wherein Ms represents methylsulfoxy group and Ph represents phenyl group)

After 42 g of the acetonide [23] described above and 20 g of potassium carbonate were stirred in 30 ml of methanol for 15 hours, the reaction solution was filtered through Celite 545. The filtrate was concentrated at 40° C. under reduced pressure and 30 ml of a solvent mixture of ethyl ether:hexane=7:3 (volume) was added to the residue. The mixture was again filtered through Celite 545 and the solvent was distilled off at 40° C. under reduced pressure. Further by distillation under reduced pressure, the crude product was obtained. The crude product was further recrystallized from bezene to give 2.7 g (yield, 21%) of (2S,3R,4R,5S) diepoxide [24].

$^1$H NMR (CDCl$_3$) δ: 1.39 (6H, s, CH$_3$×2), 2.6–2.9 (4H, m, CH$_2$×2), 2.95–3.12 (2H, m, CH), 3.7–3.95 (2H, m, CH)

iii)

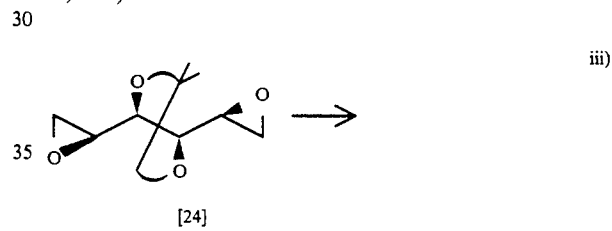

[24]

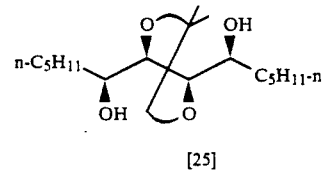

[25]

To a mixture of 320 mg of cuprous cyanide and 100 ml of anhydrous tetrahydrofuran was added 64 ml (94 mols) of an ethereal solution of n-butyl magnesium bromide having a concentration of 1.47 mol at 0° C. over 5 minutes. After stirring was continued for further 5 minutes, a solution of 6.48 g of the diepoxide [24] described above in 50 ml of anhydrous tetrahydrofuran was dropwise added to the mixture at 0° C. for 10 minutes. Stirring was continued for further an hour. After it was verified by thin layer chromatography that the reaction was completed, ammonium chloride and saturated sodium chloride aqueous solution were added to the reaction mixture. After stirring for 30 minutes, the reaction mixture was extracted with ethyl ether 3 times. The extracts were combined and washed, in sequence, with 1 N hydrochloric acid, saturated sodium bicarbonate aqueous solution and saturated sodium chloride aqueous solution. After drying over anhydrous magnesium sulfate, the solvent was distilled off under reduced pressure to give crude (6S,7R,8R,9S) diol [25].

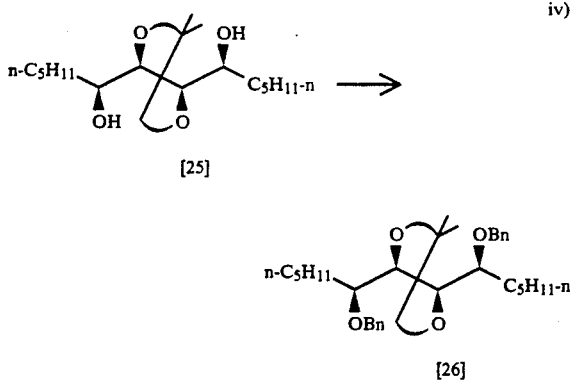

[25]

[26]

(wherein Bn represents benzyl group, hereafter the same)

After the crude diol [25] described above was dissolved in 30 ml of anhydrous tetrahydrofuran, a suspension of 0.024 g (1.07 mM) of sodium hydride in 100 ml of anhydrous tetrahydrofuran was dropwise added to the solution under reflux over 15 minutes. After stirring for further an hour under reflux, the mixture was cooled to 0° C. After 132 mg of DC-18-crown ether-6 and 9.3 ml (78 mols) of benzyl bromide were added to the suspension at 0° C., the mixture was refluxed for 4 hours while stirring. After the solvent was distilled off under reduced pressure, 1 N hydrochloric acid was added to the residue followed by extraction with hexane 3 times. The extracts were combined and sequentially washed with saturated sodium bicarbonate aqueous solution and saturated sodium chloride aqueous solution. After drying over anhydrous magnesium sulfate, the solvent was distilled off under reduced pressure to give (6S,7R,8R,9S) acetonide [26].

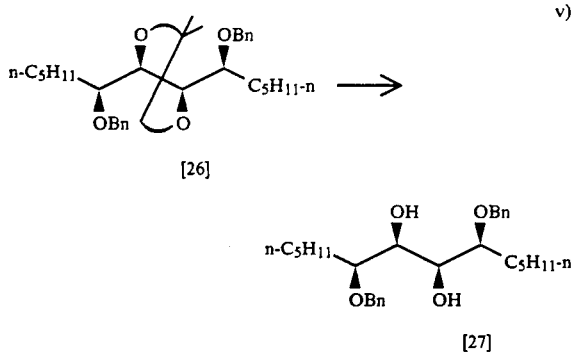

[26]

[27]

After the acetonide [26] described above was stirred at 100° C. in 100 ml of 80% acetic acid for 10 hours with heating, the solvent was distilled off under reduced pressure followed by extraction with diethyl ether. The extract was washed with sodium hydroxide aqueous solution and the aqueous phase was further extracted with diethyl ether. The extracts were combined and washed, in sequence, with 1 N hydrochloric acid, saturated sodium bicarbonate aqueous solution and then saturated sodium chloride aqueous solution, and then dried over anhydrous magnesium sulfate. After the solvent was distilled off, the residue was purified by silica gel column chromatography (eluted with ethyl ether:hexane=1:4 (volume)) to give 8.66 g of (6S,7R,8R,9S) diol [27].

$^1$H NMR (CDCl$_3$) δ: 0.88 (6H, br, CH$_3$×2), 1.0–1.8 (16H, m, CH$_2$×8), 3.4–3.7 (4H, m, CH), 4.46 (2H, d, J=10.8 Hz, CH), 4.62 (2H, d, J=10.8 Hz, CH), 7.30 (10H, s, C$_6$H$_5$)

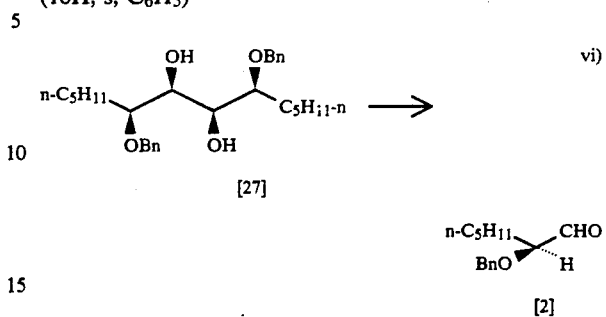

[27]

[2]

After 260 mg of lead tetraacetate was added at 4° C. to a mixture of 200 mg of the diol [27] described above, 60 mg of potassium carbonate and 4.5 ml of anhydrous benzene, the mixture was stirred for 3 minutes. After completion of the reaction, 100 ml of hexane was added to the reaction solution. The reaction solution was filtered through Celite 545 and the filtrate was washed with saturated sodium bicarbonate aqueous solution. The aqueous phase was extracted with hexane twice. The extracts were combined and washed with saturated sodium chloride aqueous solution. After drying over anhydrous magnesium sulfate, the solvent was distilled off under reduced pressure. The residue was purified by silica gel column chromatography (ethyl ether:hexane=1:2 (volume)) to give 160 mg (yield, 80%) of (S) 2-benzyloxyheptanal [2].

[α]$_D^{25}$: −83.23° (C=1.014, CHCl$_3$)

$^1$H NMR (CDCl$_3$) δ: 0.87 (3H, t, J=5.8 Hz, CH$_3$), 1.0–1.8 (8H, m, CH$_2$), 3.73 (1H, dt, J=2.2 Hz, 6.2 Hz, CH), 4.51 (1H, d, J=11.6 Hz, CH), 4.65 (1H, d, J=11.6 Hz, CH), 7.35 (5H, s, C$_6$H$_5$), 9.64 (1H, d, J=2.2 Hz)

$^{13}$C NMR δ: 13.9, 22.4, 24.4, 30.1, 31.6, 72.5, 83.6, 128.0, 128.5, 137.6, 203.5

IR (neat): 1728, 1179, 1119, 738, 698 cm$^{-1}$

EXAMPLE 1

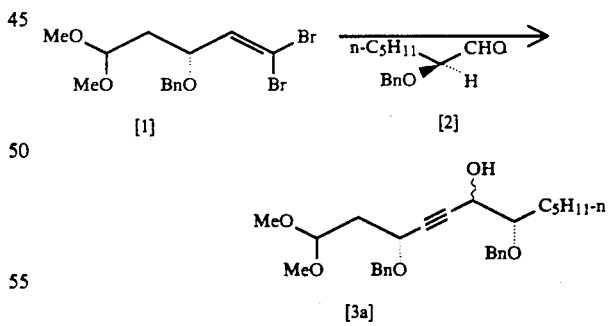

[1]

[2]

[3a]

A solution of 6.62 g (16.8 mM) of (R) 3-benzyloxy-1,1-dibromo-5,5-dimethoxypenta-1-ene [1] described above in 100 ml of anhydrous tetrahydrofuran was cooled to −78° C. and 20.8 ml (33.6 mM) of 1.62 mol/l of butyl lithium/hexane solution was dropwise added to the solution over 10 minutes under the nitrogen atmosphere. The mixture was stirred at −78° C. for an hour and at room temperature for an hour to convert the above compound [1] into (R) 3-benzyloxy-5,5-dimethoxypenta-1-yne lithium acetylide. The reaction mixture was again cooled to −78° C. and a solution of 3.61 g (16.4 mM) of (S) 2-benzyloxyheptanal [2] in 20 ml of anhydrous tetrahydrofuran was dropwise added to the reaction mixture. After stirring for further 30 minutes, ammonium chloride aqueous solution was added thereto followed by extraction with diethyl ether 3 times. The extract was then washed with saturated sodium chloride aqueous solution. After the extract was dried over anhydrous magnesium sulfate, the solvent was distilled off under reduced pressure. The residue was subjected to silica gel column chromatography and 5.73 g (12.6 mM) of (3R,7S) 3,7-dibenzyloxy-1,1-dimethoxydodeca-4-yn-6-ol [3a], which was a mixture of erythro and threo compounds, was obtained from the fraction eluted with diethyl ether:hexane=1:3. Yield, 77%.

$^1$H NMR (CCl$_4$) δ: 0.87 (3H, br t), 1.05–1.55 (8H, m), 1.77 (2H, dd, J=7 Hz), 3.18 (4H, s), 4.10–5.85 (11H, m), 7.35 (10H, s)

IR (neat): 3430, 1065, 738, 697, 595 cm$^{-1}$

EXAMPLE 2

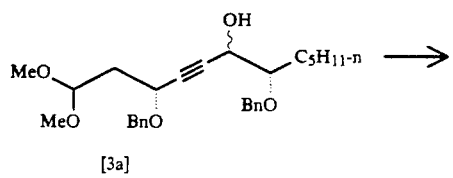

[3a]

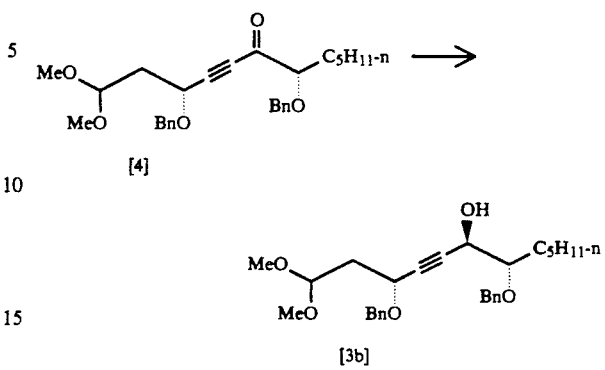

[4]

After 0.38 ml (4.4 mM) of oxalyl chloride was dropwise added to a solution of 680 mg (8.7 mM) of anhydrous dimethylsulfoxide in 15 ml of anhydrous methylene chloride at −78° C. over 5 minutes, stirring was continued for further 30 minutes at the same temperature. To the mixture was dropwise added 10 ml of a solution of 1.32 g (2.9 mM) of (3R,7S) 3,7-dibenzyloxy-1,1-dimethoxydodeca-4-yn-6-ol [3a] in anhydrous methylene chloride at the same temperature. Stirring was continued for 10 minutes at the same temperature and 2.1 ml (15.3 mM) of anhydrous triethylamine was added at once to the mixture to terminate the reaction. The mixture was poured into 1 N hydrochloric acid (6.6 mM) and the aqueous phase was extracted with methylene chloride 3 times. The extracts were combined and washed with saturated ammonium chloride aqueous solution and then saturated sodium chloride aqueous solution. After drying over anhydrous magnesium sulfate, the solvent was distilled off under reduced pressure to give 1.25 g (2.76 mM) of (3R, 7S) 3,7-dibenzyloxy-1,1-dimethoxydodeca-4-yn-5-one [4]. Yield, 95%.

[α]$_D^{25}$: +30.37° (C=1.014, CHCl$_3$)

$^1$H NMR (CDCl$_3$) δ: 0.87 (3H, br t), 1.05–1.95 (8H, m), 1.95–2.10 (2H, m), 3.26 (3H, s), 3.30 (3H, s), 3.91 (1H, t, J=6.3 Hz), 4.22–4.95 (6H, m), 7.20–7.50 (10H, m)

$^{13}$C NMR (CDCl$_3$) δ: 13.9, 22.4, 24.8, 31.5, 32.2, 38.5, 53.1, 53.5, 65.4, 71.3, 72.5, 83.4, 85.0, 93.1, 101.3, 127.9, 128.1, 128.5, 137.2, 137.5, 189.3

IR (neat): 2200, 1680, 1130, 1090, 740, 695 cm$^{-1}$

EXAMPLE 3

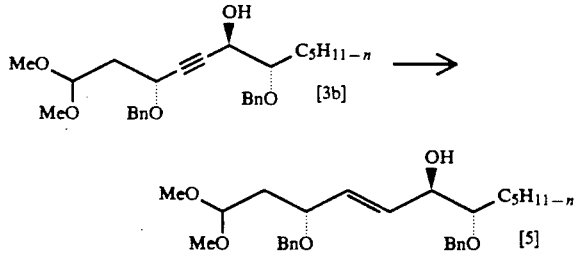

To a solution of 944 mg (2.1 mM) of (3R,7S) 3,7-dibenzyloxy-1,1-dimethoxydodeca-4-yn-5-one [4] described above in 20 ml of anhydrous diethyl ether was dropwise added 12.6 ml (3.3 mM) of 0.26 mol/l of zinc borohydride/diethyl ether solution at −30° C. over 5 minutes under the nitrogen atmosphere. Stirring was continued for 30 minutes at the same temperature. After completion of the reaction, water and 20 ml of 0.5 N hydrochloric acid were added and the resulting mixture was stirred at 0° C. for 30 minutes. The aqueous phase was extracted with diethyl ether 3 times and the extracts were combined and washed sequentially with saturated sodium bicarbonate aqueous solution and saturated sodium chloride aqueous solution. After drying over anhydrous magnesium sulfate, the solvent was distilled off under reduced pressure. The residue was subjected to silica gel column chromatography and 654 mg (1.44 mM) of (3R,6R, 7S) 3,7-dibenzyloxy-1,1-dimethoxydodeca-4-yn-6-ol [3b] was obtained from the fraction eluted with diethyl ether:hexane=1:3. Yield, 69%.

[α]$_D^{25}$: +50.59° (C=0.854, CHCl$_3$)

$^1$H NMR (CDCl$_3$) δ: 0.88 (3H, br t), 1.04–1.90 (8H, m), 1.95–2.18 (2H, m), 2.3–3.6 (1H, m), 3.27 (3H, s), 3.30 (3H, s), 3.38–3.62 (1H, m), 4.10–4.90 (7H, m), 7.2–7.6 (10H, m)

$^{13}$C NMR (CDCl$_3$) δ: 14.0, 22.5, 25.3, 30.2, 31.9, 53.1, 53.3, 64.2, 65.6, 70.7, 72.5, 81.7, 84.4, 84.7, 101.7, 127.6, 127.7, 128.0, 128.3, 128.4, 137.9, 138.3

IR (neat): 3426, 1091, 1071, 738, 698 cm$^{-1}$

EXAMPLE 4

A solution of 654 mg (1.44 mM) of (3R,6R, 7S) 3,7-dibenzyloxy-1,1-dimethoxydodeca-4-yn-6-ol [3b] described above in 10 ml of anhydrous tetrahydrofuran was dropwise added at 0° C. to a suspension of 115.7 mg (3.02 mM) of lithium aluminum hydride in 5 ml of anhydrous tetrahydrofuran, the mixture was stirred for 18 minutes under reflux. After completion of the reaction, ethyl acetate, ethanol, water and 0.1 N hydrochloric acid were added in sequence. Then, the aqueous phase was extracted with diethyl ether 3 times. The extracts were combined and washed with saturated sodium chloride aqueous solution. After drying over anhydrous magnesium sulfate, the solvent was distilled off under reduced pressure. The residue was subjected to silica gel column chromatography and 538 mg (1.18 mM) of (3R,6R,7S) 3,7-dibenzyloxy-1,1-dimethoxydodeca-4-en-6-ol [5] was obtained from the fraction eluted with diethyl ether:hexane=1:3. Yield, 82%.

$[\alpha]_D^{25}$: +28.92° (C=1.964, CHCl$_3$)

$^1$H NMR (CDCl$_3$) δ: 0.88 (3H, br t), 1.0–1.70 (8H, m), 1.70–2.04 (2H, m), 2.14–2.38 (1H, br s), 3.26 (3H, s), 3.28 (3H, s), 3.32–3.60 (1H, m), 3.76–4.06 (1H, m), 4.18–4.80 (6H, m), 5.60–5.84 (2H, m), 7.04–7.60 (10H, m)

$^{13}$C NMR (CDCl$_3$) δ: 14.0, 22.6, 25.4, 29.7, 32.0, 39.1, 52.6, 53.5, 70.3, 72.3, 72.8, 76.2, 82.3, 101.9, 127.5, 127.7, 128.3, 128.4, 131.9, 132.4, 138.5, 138.6

IR (neat): 3450, 1140–1040, 738, 698 cm$^{-1}$

EXAMPLE 5

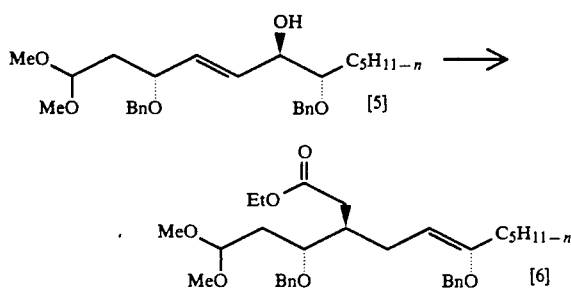

After 1.15 g (2.53 mM) of (3R,6R,7S) 3,7-dibenzyloxy-1,1-dimethoxydodeca-4-en-6-ol [5] described above, 1.65 ml (9.03 mM) of triethyl orthoacetate and a catalytic amount of heptanoic acid were reacted in 15 ml of xylene with heating at 160° C. for 20 minutes, xylene and the formed ethanol were distilled off under reduced pressure. After completion of the reaction, saturated sodium bicarbonate aqueous solution was added to the residue. The aqueous phase was extracted with diethyl ether 3 times. The extracts were combined and washed with saturated sodium chloride aqueous solution. After drying over anhydrous magnesium sulfate, the solvent was distilled off under reduced pressure. The residue was then subjected to silica gel column chromatography and 971 mg (1.85 mM) of (1'R,3S,6S) ethyl 6-benzyloxy-3-(1'-benzyloxy-3',3'-dimethoxypropyl)undeca-4-enoate [6] was obtained from the fraction eluted with diethyl ether:hexane=1:10. Yield, 73%.

$^1$H NMR (CDCl$_3$) δ: 0.87 (3H, br t), 1.00–2.00 (14H, m), 2.16–2.78 (2H, m), 3.24 (3H, s), 3.30 (3H, s), 3.44–3.82 (3H, m), 4.08 (2H, q, J=7 Hz), 4.24–4.90 (4H, m) 5.40–5.60 (2H, m), 7.12–7.60 (10H, m)

IR (neat): 1740, 1130, 1090, 740, 705 cm$^{-1}$

EXAMPLE 6

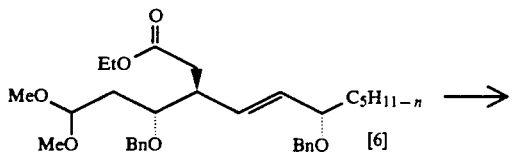

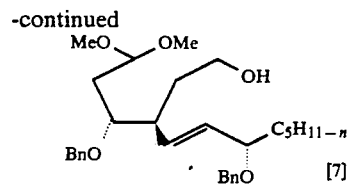

After 971 mg (1.85 mM) of (1'R,3S,6S) ethyl 6-benzyloxy-3-(1'-benzyloxy-3',3'-dimethoxypropyl)-undeca-4-enoate [6] described above was dissolved in 15 ml of anhydrous diethyl ether, 141 mg (3.7 mM) of lithium aluminum hydride was added to the solution. The mixture was stirred at room temperature for an hour. After saturated sodium sulfate aqueous solution and then 10% sodium hydroxide were added to the reaction mixture, diethyl ether solution was taken out by decantation. The remaining aluminum salt was washed with diethyl ether 5 times. These diethyl ether solutions were combined and washed with saturated sodium chloride aqueous solution. After drying over anhydrous magnesium sulfate, the solvent was distilled off under reduced pressure. The residue was subjected to silica gel column chromatography and 886 mg (1.83 mM) of (3R,4S,7S) 3,7-dibenzyloxy-4-(2'-hydroxyethyl)-1,1-dimethoxydodeca-5-ene [7] was obtained from the fraction eluted with diethyl ether:hexane=1:6 and the fraction eluted with methylene chloride. Yield, 99%.

$[\alpha]_D^{25}$: −2.19° (C=1.114, CHCl$_3$)

$^1$H NMR (CDCl$_3$) δ: 0.87 (3H, br t), 1.03–2.10 (13H, m), 2.40–2.76 (1H, br), 3.24 (3H, s), 3.29 (3H, s), 3.40–3.84 (3H, m), 4.20–4.80 (6H, m), 5.40–5.58 (2H, m), 7.06–7.56 (10H, m)

IR (neat): 3420, 1665, 1120, 1070, 729, 698 cm$^{-1}$

EXAMPLE 7

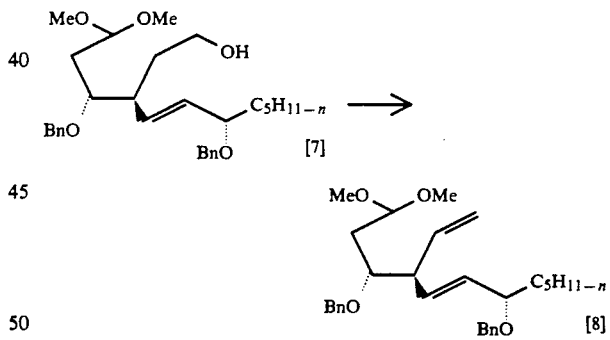

To a suspension of 997 mg (3.67 mM) of o-nitrophenylselenium cyanide in 12 ml of anhydrous tetrahydrofuran was dropwise added 886 mg (1.83 mM) of (3R,4S,7S) 3,7-dibenzyloxy-4-(2'-hydroxyethyl)-1,1-dimethoxydodeca-5-ene [7] described above. The mixture was stirred for several minutes and 0.91 ml (3.67 mM) of tri-n-butylphosphine was dropwise added to the mixture. The reaction solution was stirred for ten minutes then cooled to 0° C. and 35% hydrogen peroxide aqueous solution was dropwise added thereto at the same temperature while stirring. After stirring for 3 hours, the aqueous phase was extracted with a solvent mixture of diethyl ether:hexane=7:3. The extracts were combined and washed sequentially with saturated sodium bicarbonate aqueous solution and saturated sodium chloride aqueous solution. After drying over anhydrous magnesium sulfate, the solvent was distilled off under reduced pressure. The precipitated crystals were taken from the residue by filtration to give 776 mg (1.67 mM) of (3R,4S,7S) 3,7-dibenzyloxy-4-vinyl-1,1-dimethoxydodeca-5-ene [8]. Yield, 91%.

¹H NMR (CDCl₃) δ: 0.86 (3H, br t), 1.00-2.00 (11H, m), 3.25 (3H, s), 3.29 (3H, s), 3.46-3.86 (3H, m), 4.31, 4.58 (2H, ABq, J=11.9 Hz), 4.48, 4.84 (2H, ABq, J=11.2 Hz), 4.90-5.40 (2H, m), 5.40-6.14 (3H, m), 7.18-7.60 (10H, m)

IR (neat): 2900, 1630, 1120, 1095, 1070, 918, 730, 692 cm⁻¹

EXAMPLE 8

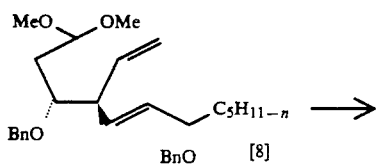

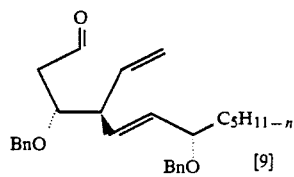

While stirring, 776 mg (1.67 mM) of (3R,4S, 7S) 3,7-dibenzyloxy-4-vinyl-1,1-dimethoxydodeca-5-ene [8] described above was heated in a mixture of 13 ml of 80% acetic acid and 2 ml of tetrahydrofuran at 40° C. for 5 hours. Completion of the reaction was confimred by thin layer chromatography. Then, the reaction solution was poured into saturated sodium bicarbonate aqueous solution. The mixture was extracted 3 times with a solvent mixture of diethyl ether:hexane=7:3. The extracts were combined and washed sequentially with saturated sodium bicarbonate aqueous solution and saturated sodium chloride aqueous solution. After drying over anhydrous magnesium sulfate, the solvent was distilled off under reduced pressure to give 701 mg (1.67 mM) of (3R,4S,7S) 3,7-dibenzyloxy-4-vinyl-dodeca-5-enecarboaldehyde [9]. Yield, 100%.

$[\alpha]_D^{25}$: +3.81° (C=1.02, CHCl₃)

¹H NMR (CDCl₃) δ: 0.84 (3H, br t), 1.06-1.80 (8H, m), 2.50-2.75 (2H, m), 2.92-3.34 (1H, m), 3.50-3.86 (1H, m), 3.88-4.16 (1H, m), 4.20-4.80 (4H, m), 4.90-5.44 (2H, m), 5.44-6.10 (3H, m), 7.05-7.50 (10H, m), 9.88 (1H, t)

¹³C NMR (CDCl₃) δ: 13.9, 22.5, 25.0, 31.6, 35.7, 46.4, 50.3, 70.1, 72.1, 80.0, 117.1, 127.3, 127.5, 127.7, 128.2, 128.3, 130.7, 134.3, 136.9, 137.9, 138.9, 200.7

IR (neat): 1730, 1100, 1070, 920, 740, 700 cm⁻¹

EXAMPLE 9

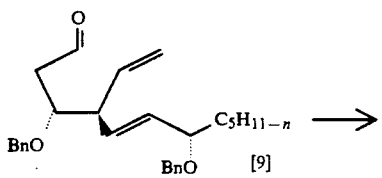

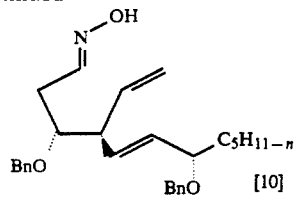

After 701 mg (1.67 mM) of (3R,4S,7S) 3,7-dibenzyloxy-4-vinyldodeca-5-enecarboaldehyde [9] described above was dissolved in 5 ml of pyridine, 138 mg (2.00 mM) of recrystallized hydroxyamine hydrochloride was added to the solution. The mixture was stirred for an hour. To the reaction solution was added 80 ml of ether. The mixture was washed with saturated sodium chloride aqueous solution 4 times. After drying over anhydrous magnesium sulfate, the solvent was distilled off under reduced pressure. The residue was subjected to silica gel column chromatography and 552 mg (1.27 mM) of (3R,4S, 7S) 3,7-dibenzyloxy-4-vinyldodeca-5-enecarboxime [10] was obtained from the fraction eluted with 12% of diethyl ether/hexane. Yield, 76%.

¹H NMR (CDCl₃) δ: 0.86 (3H, br t), 1.0-1.80 (8H, m), 2.30-2.76 (2H, m), 2.95-3.25 (1H, br q), 3.40-3.88 (2H, m), 4.18-4.76 (4H, m), 4.95-6.16 (6H, m), 7.18-7.60 (10H, m)

IR (neat): 3270, 1090-1060, 915, 738, 695 cm⁻¹

EXAMPLE 10

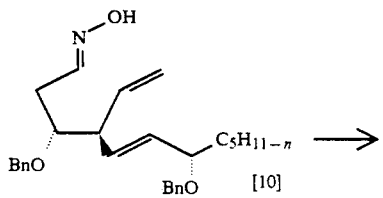

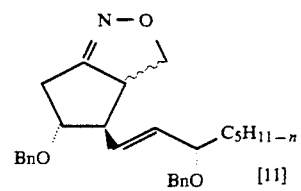

After 552 mg (1.27 mM) of (3R,4S,7S) 3,7-dibenzyloxy-4-vinyldodeca-5-enecarboxime [10] and a catalytic amount of triethylamine were dissolved in 12 ml of methylene chloride, the solution was vigorously stirred at 0° C. Then 6 ml (8.2 mM) of 10% sodium hypochlorite was dropwise added to the solution and the mixture was stirred at the same temperature for an hour. After stirring at room temperature for further 10 hours, the reaction mixture was poured into saturated sodium bicarbonate aqueous solution. The aqueous phase was extracted 3 times with a solvent mixture of diethyl ether:hexane=7:3. The extracts were combined, washed with saturated sodium chloride aqueous solution and dried over anhydrous magnesium sulfate. After the solvent was distilled off under reduced pressure, the residue was subjected to silica gel column chromatography and 400 mg (0.93 mM) of optically active isoxazole derivative [11] was obtained from the fraction eluted with diethyl ether:hexane=3:7. Yield, 73%.

$^1$H NMR (CDCl$_3$) δ: 0.87 (3H, br t), 1.0–1.80 (8H, m), 2.2–2.84 (2H, m), 2.88–3.20 (1H, m), 3.20–3.44 (1H, m), 3.44–4.00 (2H, m), 4.00–4.80 (6H, m), 5.00–5.80 (2H, m), 7.20–7.60 (10H, m)

IR (neat): 1740, 1090, 1060, 910, 730, 693 cm$^{-1}$

REFERENCE EXAMPLE 3

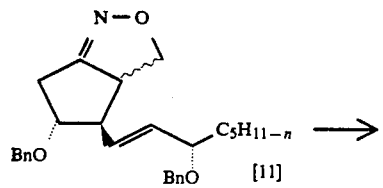

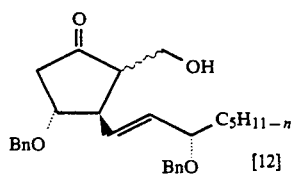

In a hydrogen gas atmosphere, 374 mg (0.86 mM) of the optically active isoxazole derivative [11] described above, 748 mg of inactivated W-2 Raney nickel and 0.86 ml of 1 mol/l hexane solution of boron trichloride were stirred in 80 ml of 80% methanol aqueous solution for 3 hours. The reaction mixture was filtered through Celite. Celite was washed with 70 ml of ethyl acetate and the filtrates were combined and poured onto a mixture of 100 ml of saturated sodium chloride aqueous solution and 400 ml of methylene chloride to perform extraction. The aqueous phase was extracted 3 times with methylene chloride. The extracts were combined and washed, in sequence, with saturated sodium bicarbonate aqueous solution and saturated sodium chloride aqueous solution and then dried over anhydrous magnesium sulfate. The solvent was distilled off under reduced pressure. The residue was subjected to silica gel column chromatography and 326 mg (0.75 mM) of optically active cyclopentanone derivative [12] was obtained from the fraction eluted with a solvent mixture of diethyl ether:hexane=6:4. Yield, 87%.

$^1$H NMR (CDCl$_3$) δ: 0.88 (3H, t, J=7.0 Hz), 1.20–1.80 (8H, m), 2.13 (1H, br t, J=5.5 Hz), 2.30 (1H, dd, J=5.5 Hz, 18.4 Hz), 2.65 (1H, d, J=18 Hz), 2.86 (1H, ddd, J=4 Hz, 9 Hz, 12 Hz), 3.65 (1H, dt, J=7 Hz, 9 Hz), 3.79 (2H, ABq), 3.94–4.02 (1H, m), 4.17 (1H, t, J=4.5 Hz), 4.35 (1H, d, J=12 Hz), 4.44 (1H, d, J=12 Hz), 4.58 (2H, dd, J=6 Hz, 12 Hz), 5.56 (1H, dd, J=9 Hz, 16 Hz), 5.93 (1H, dd, J=9 Hz, 16 Hz), 7.23–7.35 (10H, m)

IR (neat): 3640, 1740, 1090, 1065, 980, 695 cm$^{-1}$

REFERENCE EXAMPLE 4

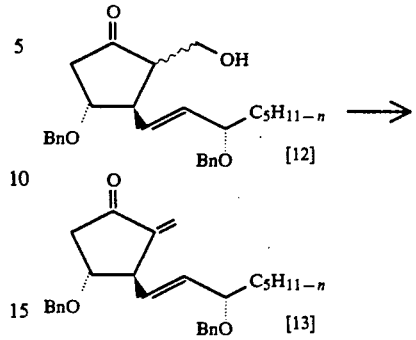

After 253 mg (0.58 mM) of the optically active cyclopentanone derivative [12] described above was dissolved in 19 ml of anhydrous pyridine, 360 μl (4.6 mM) of distilled methanesulfonyl chloride was dropwise added at 0° C. to the solution with stirring. After the mixture was stirred at the same temperature for 2 hours, the reaction mixture was poured into 0.5 N hydrochloric acid. The mixture was extracted with methylene chloride. The extract was washed, in sequence, with 0.5 N hydrochloric acid, saturated sodium bicarbonate aqueous solution and then saturated sodium chloride aqueous solution. After drying over anhydrous magnesium sulfate, the residue was subjected to high performance liquid chromatography using octadodecylated silica gel (ODS). Fractionation was carried out using 0.5% 2-propanol/hexane as an eluent to give 188 mg (0.45 mM) of optically active 2-methylenecyclopentanone derivative [13]. Yield, 78%.

[α]$_D^{25}$: −76.00° (C=0.287, CHCl$_3$)

$^1$H NMR (CDCl$_3$) δ: 0.87 (3H, br t), 1.00–1.80 (8H, m), 2.20–2.95 (2H, m), 3.24–3.66 (1H, m), 3.66–3.96 (1H, m), 3.96 (1H, dt, J=6.6 Hz, 7.3 Hz), 4.44 (1H, d, J=11.7 Hz), 4.62 (2H, s), 4.65 (1H, d, J=11.7 Hz), 5.25 (1H, d, J=2.5 Hz), 5.50–5.70 (2H, m), 6.14 (1H, d, J=2.5 Hz), 7.30 (10H, s)

IR (neat): 1731, 1640, 1095, 1027, 737, 698 cm$^{-1}$

While the invention has been described in detail and with reference to specific embodiments thereof, it is apparent to one skilled in the art that various changes and modifications can be made therein without departing from the spirit and the scope of the present invention.

What is claimed is:

1. An optically active isoxazole derivative represented by general formula:

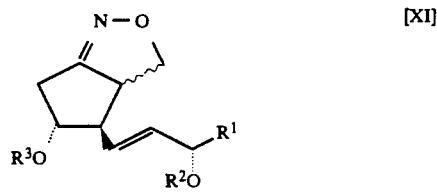

wherein R$^1$ represents an alkyl group; and R$^2$ and R$^3$, which may be the same or different, each represents an aralkyl group.

2. An optically active isoxazole derivative according to claim 1, wherein R$^1$ represents a straight or branched alkyl group having 4 to 10 carbon atoms.

3. An optically active isoxazole derivative according to claim 1, wherein R$^1$ is n-pentyl group.

* * * * *